United States Patent [19]

Knowles et al.

[11] Patent Number: 5,225,354
[45] Date of Patent: Jul. 6, 1993

[54] MONOCLONAL ANTIBODIES SPECIFIC FOR HUMAN GLYCOALBUMIN

[75] Inventors: William J. Knowles, Madison; Vincent T. Marchesi, Guilford, both of Conn.

[73] Assignee: Molecular Diagnostics, Inc., West Haven, Conn.

[21] Appl. No.: 934,085

[22] Filed: Aug. 21, 1992

Related U.S. Application Data

[60] Division of Ser. No. 518,681, May 3, 1990, which is a continuation of Ser. No. 158,200, Feb. 19, 1988, abandoned, which is a continuation-in-part of Ser. No. 54,131, Jun. 2, 1987, abandoned, which is a continuation-in-part of Ser. No. 899,456, Aug. 22, 1986, abandoned.

[51] Int. Cl.$^5$ .................. G01N 33/532; G01N 33/543
[52] U.S. Cl. ..................................... 436/548; 436/518; 436/536; 436/512; 436/63; 436/87; 436/88; 435/7.1; 435/7.92; 530/388.25
[58] Field of Search ................ 435/7.1, 7.92; 436/518, 436/536, 512, 63, 87, 548, 88, 501; 530/388.25

[56] References Cited

U.S. PATENT DOCUMENTS 4,629,692 12/1986 Dean .................... 435/7.7
4,797,473 1/1989 Tarsio et al. .................. 530/388.25

Primary Examiner—Toni R. Scheiner
Attorney, Agent, or Firm—Sprung Horn Kramer & Woods

[57] ABSTRACT

Monoclonal antibodies specific for the glycosylated lysine residue at position 525 in glycoalbumin and a method for producing such antibodies. The monoclonal antibodies are useful as reagents in immunoassays for the specific determination of glycoalbumin in human blood samples which is indicative of the severity of the diabetic condition. The monoclonal antibodies are secreted by hybridomas obtained by fusing a myeloma cell with a lymphocyte that has been taken from an animal, usually a mouse, immunized with a peptide immunogen and which produces antibody to the lysine 525 residue in glycoalbumin. The synthetic peptide immunogen comprises a peptide residue which includes an ε-amino glucosylated lysine and an adjacent amino acid sequence in which at least one of the amino acid units is in a position corresponding to the peptide sequence of human albumin adjacent to lysine 525, the glycosylated peptide residue being linked to an immunogenic carrier.

14 Claims, 8 Drawing Sheets

GLYCOALBUMIN PEPTIDES (1) ---LYS-GLU-ARG-GLN-ILE-LYS-LYS-GLN-THR-ALA-LEU-VAL-GLU-LEU-VAL-LYS-HIS-LYS---
                                                                                                       ▲(525)

TRYPTIC PEPTIDE (2) ---LYS-GLU-ARG-GLN-ILE-LYS-LYS-GLN-THR-ALA-LEU-VAL-GLU-LEU-VAL-LYS-HIS-LYS---
     (525)

V8 PEPTIDE (3) *LYS-GLU-ARG-GLN-ILE-LYS-LYS-GLN-THR-ALA-LEU-VAL-GLU-LEU-VAL-(TYR-CYS)-COOH    ALB K14C
     (525)

(4) *(CYS)-GLU-ARG-GLN-ILE-LYS-LYS-GLN-THR-ALA-LEU-VAL-GLU-LEU-VAL-GLU-LEU-COOH    ALB C11L
     (525)

(5) *GLN-ILE-LYS-LYS-GLN-THR-ALA-LEU-VAL-GLU-LEU-VAL-GLU-LEU-(CYS)-COOH    ALB Q12C
     (525)

(6) *ARG-GLN-ILE-LYS-LYS-GLN-THR-ALA-LEU-VAL-GLU-LEU-VAL-GLU-COOH    ALB R11E
     (525)

(7) *LYS-GLN-THR-ALA-LEU-VAL-GLU-LEU-VAL-(CYS)-COOH    ALB Q9C
     (525)

FIG. 1

(8) \*LYS-GLN-THR-ALA-LEU-TYR-TYR-CYS (525)    ALB Q7C
                                                                ALB K8C (9) \*LYS-LYS-GLN-THR-ALA-LEU-TYR-TYR-CYS (525)    ALB K9C

(10) \*ILE-LYS-LYS-GLN-THR-ALA-LEU-TYR-TYR-CYS (525)    ALB I10C

(11) \*GLN-ILE-LYS-LYS-GLN-THR-ALA-LEU-TYR-TYR-CYS (525)    ALB Q11C

(12) \*CYS-TYR-TYR-ARG-GLN-ILE-LYS-LYS-GLN-THR (525)    ALB C10T

FIG. 2

MONOCLONAL ANTIBODIES SPECIFIC FOR HUMAN GLYCOALBUMIN

CROSS REFERENCE TO RELATED APPLICATIONS

This is a division of application Ser. No. 07/518,681, filed May 3, 1990, pending which is a continuation of Ser. No. 07/158,200, filed Feb. 19, 1988, now abandoned; which is a continuation-in-part of Ser. No. 07/054,131, filed Jun. 2, 1987, now abandoned; which is a continuation-in-part of Ser. No. 06/899,456, filed Aug. 22, 1986, now abandoned.

BACKGROUND OF THE INVENTION

This invention relates to the determination of the glycosylated form of albumin, herein referred to as glycoalbumin, in human blood samples. The determination of the extent of glycosylation of albumin in an individual's blood provides a useful index of glucose level control in diabetics. In particular, the present invention concerns the preparation of monoclonal antibodies which recognize specifically the glycosylated lysine residue at position 525 in human albumin.

Albumin is the major serum protein of blood and has a half life in circulation of 10 days. A non-enzymatic glycosylation reaction results in the covalent coupling of glucose to a small percentage of albumin molecules in all individuals. Since the rate of non-enzymatic glycosylation is dependent upon the circulating level of glucose, diabetics having a higher average level of blood glucose, have an increase in glycosylated albumin. The severity of the diabetic condition is therefore reflected in the percentage of glycosylated albumin.

An analogous reaction occurs between glucose and hemoglobin producing hemoglobin Alc plus other glycosylated hemoglobins. Hemoglobin has a life of 120 days, therefore determination of glycosylated hemoglobin values reflects the average circulating glucose level for that period, whereas a glycoalbumin determination will represent an average circulating glucose level of 10 days. The importance of glycosylated hemoglobin values have been widely accepted as being clinically important for accurate assessment of the diabetic condition. Assays for glycosylated hemoglobin were relatively easy to develop because the hemoglobin molecule is colored and therefore is easy to quantitate using inexpensive spectrophotometers. Albumin is colorless and methods for quantitation of glycoalbumin require that the carbohydrate be derivatized to a colored product or that the protein portion of glycoalbumin be reacted to produce a colored product. For this reason there are no glycoalbumin assays in large scale use in clinical labs at the present time.

A number of proposed glycoalbumin assays are known from the literature. Principal among these are those based on boronate chromatography and thiobarbituric assays. The boronate chromatography method includes the colorimetric determination of bound protein, e.g., bound to Glycogel of Pierce Chemical Co. In this assay, serum is applied to a boronate affinity column wherein all cis-diol containing substances (e.g., glycoalbumin and other glycoproteins) are bound. These substances are then eluted and both bound and eluate fractions quantitated after adding a dye that reacts with proteins producing a colored product. The major disadvantages of this method are that many non-albumin proteins in serum are glycoproteins (e.g., immunoglobulins) and are therefore bound and measured in the boronate chromatography assay; the column procedure has multiple steps for separation and analysis and is not easily automated; and there is also data suggesting that glucose interfers with boronate binding. In the thiobarbituric assay, the ketoamine-protein adduct is converted to 5-hydroxymethylfurfural by hydrolysis with oxalic acid yielding a colored product. The major disadvantages here are that hydrolysis requires 2-4 hours at 100° C. or higher; background color must be corrected; and at the present time, standards or calibrators are not available.

The reaction of glucose with albumin involves (a) the formation of a Schiff's base between C-1 of the glucose with an amino group of albumin and (b) an Amadori rearrangement producing a 1-deoxyfructosyl carbohydrate covalently coupled to the nitrogen of the amino group. The albumin molecule has 60 potential sites (amino groups) for non-enzymatic glycosylation. This is comprised of 59 episilon amino groups of lysine residues and one alpha amino group on the N-terminus of the protein. Of the 60 potential sites only one lysine is known to be glycosylated in the native molecule; however, other lysines may be glycosylated to various extents. The known lysine has been identified as lysine 525 (the 525th amino acid counting from the N-terminus of the protein - Garlick et al, J. Biol. Chem. 258: 6142 (1983)) and the position has been confirmed herein. The reason for the specific glycosylation of this lysine and the rapid rate of glycosylation of albumin is not entirely clear. The specificity for lysine 525 is likely to be (a) the proximity to an adjacent lysine at position 524 thereby lowering the pKa of the $\epsilon$-amino group of lysine 525 making it more reactive in the glycosylation reaction, (b) the exposure of the lysine 525 side chain to the aqueous exterior of the albumin molecule, and/or (c) the 3-dimensional structure of the albumin molecule that by an unknown mechanism increases the reactivity of lysine 525 for the glycosylation reaction.

Monoclonal antibodies have been shown to have a precise specificity for binding to a variety of organic compounds, including synthetic peptides. However, despite the availability of this technique and the recognized need for an immunoassay for glycoalbumin, an approach to obtaining antibodies useful for the determination of glycoalbumin has not been reported.

The following definitions will be used herein with respect to amino acid units in peptides.

| Definitions | |
| --- | --- |
| Amino Acid | Abbreviation |
| Arginine | Arg |
| Aspartic Acid | Asp |
| Glutamic Acid | Glu |
| Lysine | Lys |
| Serine | Ser |
| Asparagine | Asn |
| Glutamine | Gln |
| Glycine | Gly |
| Proline | Pro |
| Threonine | Thr |
| Alanine | Ala |
| Histidine | His |
| Cysteine | Cys |
| Methionine | Met |
| Valine | Val |
| Isoleucine | Ile |
| Leucine | Leu |
| Tyrosine | Tyr |
| Phenylalanine | Phe |

| Definitions | |
|---|---|
| Amino Acid | Abbreviation |
| Tryptophan | Trp |
| Alpha-Aminobutyric Acid | Aba |

SUMMARY OF THE INVENTION

It is therefore an object of the present invention to provide antibodies specific for binding to glycoalbumin which can serve as the basis of an immunoassay to determine glycoalbumin in human blood samples. There is a well recognized but unresolved need for such an immunoassay which would provide a relatively simple and reliable means for assessing the diabetic condition.

It is particularly an object of the present invention to raise monoclonal antibodies that bind specifically to human albumin that is glycosylated at the lysine residue at position 525, i.e., the 525th amino acid in the peptide chain counting from the end having the free N-terminal amino group. As used herein, a glycosylated amino acid refers to an amino acid having an amino group that has been modified with a 1-deoxyfructosyl residue by nonenzymatic reaction with glucose.

The present invention accomplishes these and other objectives and advantages by providing a method for obtaining somatic cell hybridomas that secrete monoclonal antibodies having the desired glycoablumin specificity. Such hybridomas are formed from conventional fusions of myeloma cells with lymphocytes from an animal, preferably a mouse, that has been immunized with an immunogen comprising an appropriate glycosylated peptide chemically linked to an immunogenic carrier material. The glycosylated peptide in the immunogen is obtained synthetically or by proteolysis and comprises first, a lysine residue whose ε-amino group is nonenzymatically glycosylated, and second, at least one other amino acid unit in a position corresponding to the peptide sequence of human albumin adjacent to the lysine residue at position 525.

Accordingly, the monoclonal antibody of the present invention binds specifically to a glycosylated peptide residue of the formula:

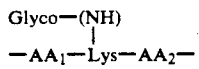

wherein Glyco-(NH) represents a nonenzymatically glycosylated ε-amino group in the lysine residue, and one or both of $AA_1$ and $AA_2$ is a sequence of amino acids, preferably containing between 1 and 12 amino acids, wherein at least one, and preferably all, of the amino acid units is in a position corresponding to the peptide sequence of human albumin adjacent to lysine 525, and if only one of $AA_1$ and $AA_2$ is such a sequence, then the other is a bond, a terminal amino or carboxyl group, or additional amino acid residues.

The present invention is further directed to a method of producing a hybridoma cell line which secretes a monoclonal antibody which binds specifically to the denatured form of human albumin that is glycosylated at the lysine residue at position 525, comprising the steps of;

(a) immunizing a mouse that is less than about 8 weeks old with an immunogen of the formula:

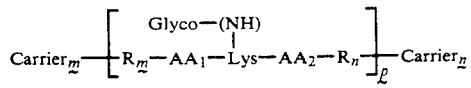

wherein Glyco-(NH) represents a nonenzymatically glycosylated ε-amino group in the lysine residue; one or both of $AA_1$ and $AA_2$ is a sequence of amino acids wherein at least one of the amino acid units is in a position corresponding to the peptide sequence of human albumin adjacent to the lysine residue at position 525, and if only one of $AA_1$ and $AA_2$ is such a sequence, then the other is a bond, a terminal amino or carboxyl group, or additional amino acid residues; R is a bond or linking group; Carrier is an immunogenic carrier material; one of $m$ and $n$ is 1 and the other is zero; and $p$ is on the average from 1 to the number of available coupling sites on Carrier;

(b) fusing lymphocytes from the immunized mouse which produce antibodies to denatured glycosylated human albumin with murine myeloma cells to form hybridomas;

(c) cloning the hybridomas on culture media selective therefor;

(d) determining an isolated hybridoma which secretes antibody specific for denatured glycosylated human albumin; and (e) subcloning such isolated hybridoma.

In addition to the above described monoclonal antibodies, including fragments thereof which comprise an antibody combining site, the hybridoma cell lines that secrete such antibody, the method for producing monoclonal antibodies from such cell lines, and the method for obtaining the cell lines and the immunogens used in such process, the present invention also provides an immunoassay method for determining glycoalbumin in a human blood sample such as whole blood, serum, or plasma. In the method, the blood sample is contacted with the monoclonal antibody or fragment thereof of the present invention. Where necessary or desirable, the blood sample is first treated to denature or otherwise expose the epitope at lysine 525 in a significant amount of any glycoalbumin present in the sample. Thereafter, the binding of the antibody reagent to glycoalbumin from the sample is determined following any conventional immunoassay protocol as a function of the amount of glycoalbumin in the sample tested. The present invention also provides new and useful peptides and glycosylated forms thereof prepared synthetically or by proteolysis of glycoalbumin or non-glycosylated albumin which can serve as the peptide residue in the immunogen or which are precursors thereof.

BRIEF DESCRIPTION OF THE DRAWINGS

FIGS. 1 and 2 of the drawings illustrate some of the preferred glycosylated peptide fragments or residues that can be linked to a conventional immunogenic carrier material to form an immunogen useful in the present invention. Structures (1) and (2) show the partial sequence of glycoalbumin in the region of lysine 525 and the sites of cleavage for the proteolytic enzymes trypsin (solid triangles) and V8 protease (open triangles), respectively. The asterisk above lysine 525 indicates the site of in vivo glycosylation. Structures (3) through (12) show peptide fragments that can be prepared synthetically. The asterisks other than at lysine 525 indicate sites of potentially additional glycosylation during in vitro synthesis. The sequences are shown in the drawing, as well as throughout this description, from N-terminus on the left to C-terminus on the right. Further details and explanations are given in the Examples below.

DESCRIPTION OF THE PREFERRED EMBODIMENTS

Figure 3:
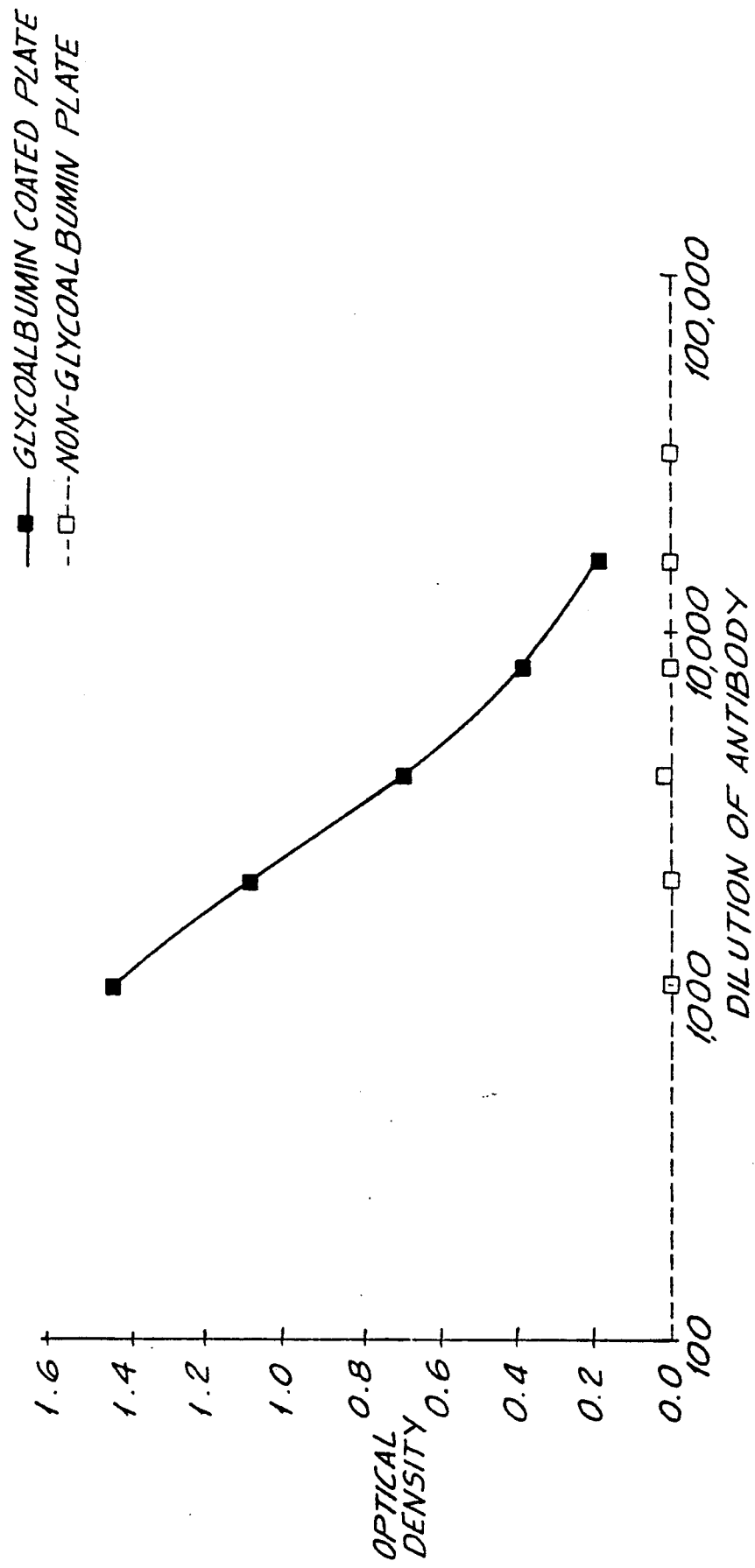
FIGS. 3, 4, 5, 6, 7 and 8 show graphical representations of results obtained using a particular monoclonal antibody obtained according to the present invention. Details of the experiments that were performed are provided in the Examples below.

The monoclonal antibody of the present invention is principally characterized by its specificity for binding the glycosylated peptide sequence in the region of lysine 525 in human albumin. This glycosylated residue is the distinguishing structural feature of glycoalbumin. An antibody of the present invention requires an epitope or determinant site comprising minimally the 1-deoxyfructosyl modified lysine unit, formed upon Amadori rearrangement of the reaction product between glucose and the ε-amino group in lysine, and a peptide sequence extending therefrom comprising at least one of the amino acid units in the position corresponding to the glycoalbumin sequence adjacent to lysine 525. The other amino acid units in the peptide sequence characterizing the epitope may be the same or different as those appearing in the native glycoalbumin sequence. In this way, the epitope is characterized as being comprised of a carbohydrate and peptide sequence to which the antibody binds and is unique to the glycosylated lysine 525 sequence in glycoalbumin. Preferably the antibody will specifically bind a glycosylated peptide residue of the formula:

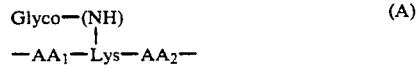

(A)

wherein Glyco-(NH), $AA_1$ and $AA_2$ are as defined above. It is minimally required that at least one of the amino acid sequences $AA_1$ and $AA_2$ comprise an amino acid in a position corresponding to the sequence in glycoalbumin around lysine 525 in order that the antibody binding be specific for glycosylation at lysine 525 rather than any other glycosylated lysine unit in glycoalbumin or any other protein or peptide that might appear in the test sample. Preferably one or both of $AA_1$ and $AA_2$ is a sequence of from 1 to 12 amino acids that correspond exactly to the peptide sequence adjacent to the lysine residue at position 525 in glycoalbumin.

The sequence of glycoalbumin including 12 amino acids on either side of lysine 525 is as follows (in the direction of N-terminus to C-terminus):

—Ile—Cys—Thr—Leu—Ser—Glu—Lys—
—Glu—Arg—Gln—Ile—Lys—Lys(525)—
—Gln—Thr—Ala—Leu—Val—Glu—Leu—
—Val—Lys—His—Lys—Pro—

Most preferably the monoclonal antibody of the present invention will bind specifically to peptide residues of formula (A) above wherein $AA_1$ and $AA_2$ are selected from the following:

$AA_1$: —Lys—Glu—Arg—Gln—Ile—Lys—,
—Glu—Arg—Gln—Ile—Lys—,
—Arg—Gln—Ile—Lys—,
—Gln—Ile—Lys—,
—Ile—Lys—,
Lys—, or a bond, and $AA_2$: —Gln—Thr—Ala—Leu—Val—Glu—
—Gln—Thr—Ala—Leu—Val—
—Gln—Thr—Ala—Leu—
—Gln—Thr—Ala—
—Gln—Thr—
—Gln—, or a bond.

In accordance with the present invention, hybridoma cell lines are raised to produce antibodies only against the glycosylated lysine 525 portion of the albumin molecule rather than to the entire protein and such cell lines and their antibodies are screened to identify and isolate those monoclonal antibodies which will thereafter react selectively with the glycosylated lysine 525 epitope.

To produce such antibodies, a fragment of the protein chain, corresponding to the naturally occurring glycosylated peptide sequence, is coupled to a carrier and injected into a laboratory animal to elicit an immune response.

Competent host animals will be any which are capable of producing lymphocytes that will fuse with myeloma or other malignant or in vitro proliferable cells, or that are otherwise manipulable, to yield a hybrid cell line, e.g., a hybridoma, that produces essentially monoclonal immunoglobulin. Under the current advancement in that art, such animals include mice and rats. Animals such as mice and rats have circulating normal albumin similar in structure to human albumin. Accordingly, it has been found to be preferred to immunize young animals in order to increase the likelihood of an immunogenic response to the present immunogens since they bear a close resemblance to the animal's native serum albumin. Young animals, particularly mice less than about 8 weeks old, and usually between about 6 and 8 weeks old, would be expected to have an immature immune response and thus more likely to react to self-antigens or antigens having structure similar to their own proteins.

Lymphocytes such as spleen cells from the immunized animal are fused with myeloma cells to produce hybridomas which are cultured and screened for production of monoclonal antibodies. The monoclonal antibodies are screened for those selective to the glycosylated peptide epitope.

It is particularly preferred in the context of the present invention to screen the monoclonal antibody-producing hybridomas with denatured glycoalbumin or fragments thereof, or with synthetic glycopeptides that mimic the structure of the carbohydrate epitope in a denatured form of albumin. Means for denaturing glycoalbumin are discussed in more detail hereinafter. The preparation of synthetic glycopeptides will follow the methods described herein for making such peptides for use in preparing immunogens. A likely immune response to the present immunogens will be directed more favorably against a non-native form, e.g., denatured or fragmented form, of the antigen.

Finally, the particular cell line is cloned for use in producing further quantities of the monoclonal antibody. Reviews of such monoclonal antibody techniques are found in Lymphocyte Hybridomas, Melchers et al, Springer-Verlag (New York 1978), Nature 266:495 (1977), Science 208:692 (1980), and Methods in Enzymology 73(Part B): 3–46 (1981).

To prepare a suitable immunogen for injection into the laboratory animal, e.g., BALB/c mice, rats or the like, a glycosylated albumin fragment must be either produced and isolated from naturally occurring human albumin or glycoalbumin or be chemically synthesized and purified. The glycosylated peptide fragment useful in the present invention, and its non-glycosylated forms or precursors, is of the formula:

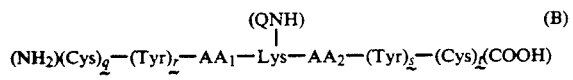

wherein at least one of $AA_1$ and $AA_2$ is a sequence of from 1 to 12 amino acids corresponding to the peptide sequence adjacent to lysine 525 in human albumin, and if only one of $AA_1$ and $AA_2$ is such a sequence, then the other is a bond; wherein $q$ and $t$ are independently zero or 1; wherein $r$ and $s$ are, independently, zero, 1 or 2; wherein QNH represents the ε-amino group in lysine and Q is hydrogen or 1-deoxyfructosyl; and wherein the N-terminal amino group in $(NH_2)AA_1$ and any lysine units in $AA_1$ or $AA_2$ can be glycosylated or non-glycosylated. Preferably Q is the only glycosylation in the fragment. Normally, if one of $q$ and $t$ is 1 then the other is zero, and further when $q$ or $t$ is zero then $r$ or $s$, respectively, is also zero.

In a preferred embodiment, glycoalbumin is isolated from human blood and cleaved with an appropriate protease enzyme or enzymes to yield appropriately sized peptide fragments comprising glycosylated lysine 525 and adjacent amino acids. Because albumin is substantially resistent to proteolysis in its native conformation, it will normally be required to denature the protein to an extent necessary for the desired proteolysis to occur. The resulting glycopeptide fragments are isolated by conventional methods such as chromatography on gels having selective affinity for carbohydrate residues and high performance liquid chromatography (HPLC). Preparation of non-glycosylated peptide fragments by cleavage of non-glycosylated albumin with subsequent glycosylation of the fragments is also possible but obviously much less desirable because of the potential for glycosylation at sites in addition to lysine 525, e.g., other lysine units and the N-terminal amino group. The preferred glycosylated peptide fragments prepared by proteolysis of human albumin are:

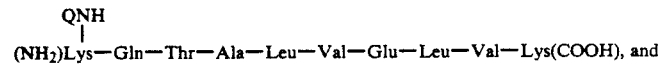

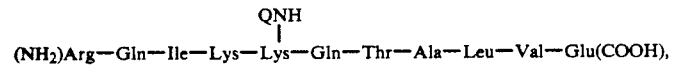

wherein Q is 1-deoxyfructosyl. Chemical synthesis can also be used to prepare peptide fragments of desired sequence following conventional procedures and using commercially available peptide synthesis instrumentation. Following peptide synthesis, the resulting peptide is glycosylated under appropriate conditions, e.g., glucose-saturated methanol or pyridine, or glucose-saturated pyridine:acetic acid (1:1) for 48 hours at room temperature. During such in vitro glycosylation, the N-terminal amino group and the ε-amino groups of all lysine units in the particular peptide including and in addition to the one corresponding to lysine 525 can be glycosylated. Such additional glycosylation can variously be tolerated during immunization by the animal responding non-specifically with respect to such glycosylation, due to the distal position of such glycosylation or its orientation in the peptide fragment, or can be selectively removed such as by protease cleavage of one or more terminal amino acids, particularly the potentially glycosylated N-terminal amino acid. The preferred glycosylated and non-glycosylated peptide fragments prepared by peptide synthesis are:

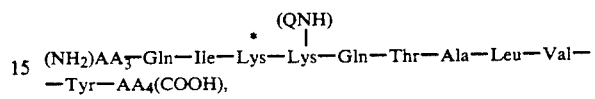

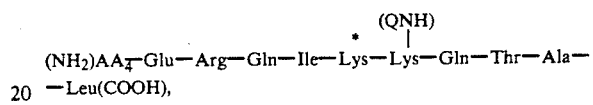

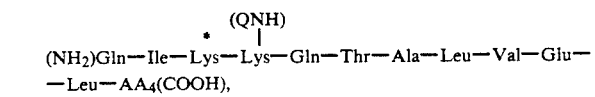

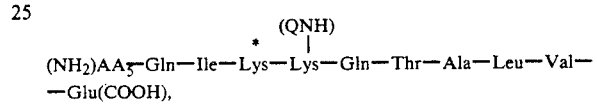

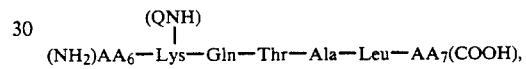

and

wherein Q is hydrogen or 1-deoxyfructosyl; $AA_3$ is Lȳs-Glu-Arg, Arg, or a bond; $AA_4$ is Cys or a bond; $AA_5$ is Arg or a bond; $AA_6$ is Gln-Ile-Lȳs, Ile-Lȳs, Lȳs, or a bond; $AA_7$ is Tyr-Tyr-Cys, Tyr-Cys, Cys or a bond; $AA_8$ is Cys-Tyr-Tyr, Cys-Tyr, Cys, or a bond; and wherein the N-terminal amino group and any Lȳs units in the peptide are glycosylated or non-glycosylated. The most useful glycosylated peptides of the above formulae will have Q being 1-deoxyfructosyl and the N-terminal amino group and any other Lys units non-glycosylated.

The preferred non-glycosylated precursor peptides are of the formulae:

Lys—Glu—Arg—Gln—Ile—Lys—Lys—Gln—Thr—Ala—

—Leu—Val—Tyr—Cys, Cys—Glu—Arg—Gln—Ile—Lys—

—Lys—Gln—Thr—Ala—Leu, Gln—Ile—Lys—Lys—

—Gln—Thr—Ala—Leu—Val—Glu—Leu—Cys, and

Lys—Gln—Thr—Ala—Z—Tyr—Tyr—Cys, Lys—Lys—Gln—

-continued

Thr—Ala—Z—Tyr—Tyr—Cys, Ile—Lys—Lys—Gln—Thr—

Ala—Z—Tyr—Tyr—Cys, Gln—Ile—Lys—Lys—Gln—Thr—

Ala—Z—Tyr—Tyr—Cys, and Cys—Tyr—Tyr—Arg—Gln—

Ile—Lys—Lys—Gln—Thr, where Z is a bond or Leu.

Particular success has been achieved using the peptide Gln-Ile-Lys-Lys-Gln-Thr-Ala-Leu-Tyr-Tyr-Cys. This peptide has the advantages of having excellent solubility in aqueous and organic buffers important for purification, glycosylation, and coupling to carriers, is readily glycosylated and the glycosylation can be readily quantitated by amino acid sequence, and has optimal size and immunogenicity for production of glycoalbumin specific antibodies. In its glycosylated form, modified at the second Lys, the resulting carbohydrate-lysine epitope that characterizes glycoalbumin is optimally exposed in the peptide for production of specific antibodies. Since the average epitope is understood to constitute 4-6 amino acids in size, the above peptide comprising 8 amino acids corresponding to the sequence in glycoalbumin can generate antibodies that require the amino acid sequence on the N-terminal, the C-terminal, or both sides of the carbohydrate-lysine residue. The restricted size of the peptide focuses the antibody binding site to the desired epitope. Therefore, a greated percentage of monoclonal antibodies against the glycopeptide will absolutely require the carbohydrate of lysine 525 as part of the epitope and will react with glycoalbumin.

A more specific glycosylation of the lysine corresponding to lysine 525 is obtained by combinations of solution and solid phase peptide synthesis coupled with α-amino blocked, ε-amino 1-deoxyfructosyl lysine. In this synthesis, $AA_2\text{-}(Tyr)_r\text{-}(Cys)_s\text{-}(COOH)$ is prepared by conventional synthesis. Lysine (α-amino blocked ε-deoxyfructosyl lysine) is prepared separately and is coupled using classical solution phase chemistry to the amino terminus of such peptide producing

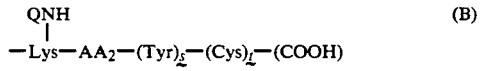
(B)

where B is a blocking group on the α-amino group of lysine, such as t-butyloxycarbonyl (t-BOC); dinitrophenyl (DNP); p-fluorenylmethoxycarbonyl (fMOC); or other suitable blocking groups which can be removed without altering the QHN-Lys (1-deoxyfructosyl lysine). The blocking group can be removed by selected chemistries (based on the particular blocking group) that do not alter the 1-deoxyfructosyl structure of lysine. This peptide can be used directly as an immunogen or in an immunoassay or can be extended by the addition of $NH_2\text{-}(Cys)_q\text{-}(Tyr)_r\text{-}AA_1$ to produce

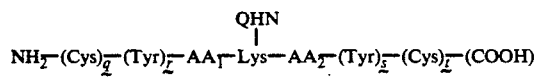

The addition can be by a sequential extension using classical solution or solid phase peptide synthesis or by a segment condensation where preformed $NH_2\text{-}(Cys)_q\text{-}(Tyr)_r\text{-}AA_1$ is condensed onto $QHN\text{-}Lys\text{-}AA_2\text{-}(Tyr)_s\text{-}(Cys)_t\text{-}(COOH)$ to yield the final product.

The introduction of terminal Cys units enables the selective coupling of the peptide to immunogenic carrier materials, such as through bifunctional linking agents well known in the art, e.g., m-maleimidobenzoyl-N-sulfosuccinimide ester (MBS). Alternatively, the peptide fragments can be coupled through the C-terminal carboxyl group using conventional peptide condensation methods, e.g., carbodiimide coupling reagents. Other linking methods conventionally known can also be used.

It will also be generally preferred to introduce one, two, or more Tyr units either as terminal units on the peptide or adjacent to the albumin-specific sequence and/or the terminal amino acid used for the coupling of the peptide to immunogenic carrier materials, e.g., adjacent to a terminal Cys unit. The presence of Tyr units in the non-specific region of the peptide residue is believed to enhance the immunogenicity of the glycosylated specific region of the peptide thereby stimulating the antibody response.

Therefore, in particularly preferred embodiments $AA_1$ and $AA_2$ in the formulas herein will, respectively, begin with the sequence $Cys\text{-}(Tyr)_r\text{-}$ and end with the sequence $\text{-}(Tyr)_s\text{-}Cys$, where $r$ and $s$ are integers from 1 to as many as 10 or more, preferably 1 or 2.

The immunogen used to stimulate production of appropriate immunoglobulins in the most general sense will comprise one or more of the glycosylated peptide residues chemically linked to an immunogenic carrier material. The general formula for such immunogen is:

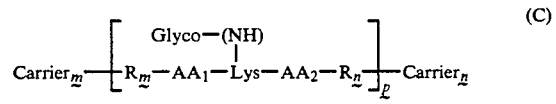
(C)

wherein Glyco-(NH), $AA_1$ and $AA_2$ are as defined previously provided that $AA_1$ and $AA_2$ can be terminal amino or carboxyl groups when m or n is zero, respectively; R is a bond or linking group; Carrier is an immunogenic carrier material; one of $m$ and $n$ is 1 and the other is zero; and $p$ is on the average from 1 to the number of available coupling sites on Carrier. The residues $AA_1$ and $AA_2$ can include Tyr and Cys units as discussed above.

The immunogenic carrier material can be selected from any of those conventionally known having functional groups available for coupling to the glycosylated peptide residue. In most cases, the carrier will be a protein or polypeptide, although other materials such as carbohydrates, polysaccharides, lipopolysaccharides, nucleic acids, and the like of sufficient size and immunogenicity can likewise be used. For the most part, immunogenic proteins and polypeptides will have molecular weights between 4,000 and 10,000,000, preferably greater than 15,000, and more usually greater than 50,000. Generally, proteins taken from one animal species will be immunogenic when introduced into the blood stream of another species. Particularly useful proteins are albumins, globulins, enzymes, hemocyanins, glutelins, proteins, having significant nonproteinaceous constituents, and the like. Further reference for the state-of-the-art concerning conventional immunogenic carrier materials and techniques for coupling haptens thereto may be had to the following: Parker, Radioimmunoassay of Biologically Active Compounds, Prentice-Hall (Englewood Cliffs, N.J. USA, 1976); Butler, J. Immunol. Meth. 7:1-24(1976); Weinryb and Shroff, Drug Metab. Rev. 10:271-283(1974); Broughton and Strong, Clin. Chem. 22:726-732(1976); and Playfair et al, Br. Med. Bull. 30:24-31(1974).

The letter p in formula (C) represents the number of glycosylated residues that are conjugated to the carrier, i.e., the epitopic density of the immunogen, and will range from 1 to the number of available coupling sites on the carrier and can be as high as 5000 in the case of certain high molecular weight synthetic polypeptides such as polylysine. The epitopic density on a particular carrier will depend upon the molecular weight of the carrier and the density of available coupling sites. Optimal epitopic densities, considering the ease and reproducibility of synthesis of the immunogen and antibody response, fall between about 10% and about 50% of the available coupling groups on the carrier involved.

Linking group R can be essentially any convenient and stable structure. Such linking group R will usually be in the form of a bond or an aliphatic chain comprising between 1 and about 20 atoms, excluding hydrogen, and including heteroatoms such as nitrogen, oxygen, and sulfur. The glycosylated residue can be joined through a variety of groups to form linking chain R, including methylene, ether, thioether, imino, and the like. One skilled in the art will have a wide variety of linking groups from which to choose to prepare the immunogen. Normally, the glycosylated peptide will be prepared terminating in a functional group such as amino, carboxyl, thiol, hydroxyl, or maleimido which is active in a coupling reaction to an appropriate group in the carrier molecule.

Particularly preferred immunogens of formula (C) are those wherein:
(a) $AA_1$ is a terminal amino group, $AA_2$ is Gln-Thr-Ala-Leu-Val-Glu-Leu-Val-Cys, $m$ is zero, and $n$ is 1;
(b) $AA_1$ is $(NH_2)$Arg-Gln-Ile-Lys, $AA_2$ is Gln-Thr-Ala-Leu-Val-Glu, $m$ is zero, and $n$ is 1;
(c) $AA_1$ is $(NH_2)$Lẏs-Glu-Arg-Gln-Ile-Lẏs, $AA_2$ is Gln-Thr-Ala-Leu-Val-Tyr-Cys, $m$ is zero, and $n$ is 1;
(d) $AA_1$ is Cys-Glu-Arg-Gln-Ile-Lẏs and $AA_2$ is Gln-Thr-Ala-Leu(COOH), $m$ is 1, and $n$ is zero; wherein Lẏs is a glycosylated or non-glycosylated lysine unit;
(e) $AA_1$ is Gln-Ile-Lys, Ile-Lys, Lys, or a terminal amino group, $AA_2$ is Gln-Thr-Ala-Leu-Tyr-Tyr-Cys, $m$ is zero, and $n$ is 1;
(f) $AA_1$ is Cys-Tyr-Tyr-Arg-Gln-Ile-Lys, $AA_2$ is Gln-Thr, $m$ is 1, and $n$ is zero.

Particular success has been attained with immunogens of formula (C) where $AA_1$ is Gln-Ile-Lys, $AA_2$ is Gln-Thr-Ala-Leu-Tyr-Tyr-Cys, $m$ is zero and $n$ is 1.

An alternative, but generally less desirable, approach to preparing the monoclonal antibodies of the present invention involves immunization with a denatured or digested form of glycoalbumin or a fragment thereof rather than with synthetic peptide immunogens as outlined above. The denatured or digested glycoalbumin can be obtained in any convenient manner including the methods discussed hereinbelow. Such denaturation should generally be sufficient to expose the carbohydrate epitope at lysine 525 in a way that the immunized animal responds immunogenically.

The antibody selected for use in an immunoassay can be of any immunoglobulin class, e.g., IgG, IgM, and so forth, and of any subclass thereof.

It may happen that the screening of hybridomas yields a cell line that produces a glycoalbumin-specific antibody of a class other than IgG, which is most preferred for use as an assay reagent for reasons of its ease of purification and its stability and well-characterized behavior in immunoassays. If considered desirable or necessary, such a hybridoma that produces non-IgG antibody, e.g., an IgM antibody, can be manipulated to become IgG-producing by a variety of known methods. For example, an immunoassay such as ELISA for detection of IgG can be used to screen for the spontaneous genetic rearrangement of IgM-producing cell lines to IgG-producing cell lines.

Normally, the antibody will be of the IgG class and if desirable any fragment of such antibody can be used which contains an antibody combining site, e.g., Fab, F(ab'), and F(ab')$_2$. The selected antibody reagent can be used in any immunoassay method for the purpose of determining glycoalbumin in a biological fluid. Such immunoassay methods include the more classical techniques such as immunodiffusion, immunoelectrophoresis, agglutination techniques, and complement fixation, as well as more current techniques involving the use of specifically detectable labels such as radioimmunoassay and nonradioisotopic methods. The latter techniques can be practiced in a wide variety of formats such as the competitive binding format in which a labeled reagent is made to compete with the glycosylated analyte for binding to the antibody reagent. The amount of labeled reagent bound to the antibody reagent, or the free-species, consisting of the labeled reagent which is not so bound, is measured appropriately and can be functionally related to the amount of glycosylated analyte in the sample.

In radioimmunoassays, the free-species and bound-species must be physically distinguished or separated in order to measure the label since the signal generated by the label is qualitatively the same in both species. Such a technique is known in the art as heterogeneous because of the phase separation requirement. Other heterogeneous immunoassay techniques are known including enzyme-labeled immunoassays, sometimes referred to as ELISA techniques (see U.S. Pat. No. 3,654,090), and fluorescent immunoassays (see U.S. Pat. Nos. 4,201,763; 4,133,639 and 3,992,631), particularly particle concentration fluorescent immunoassays (see published European Patent Application 124,050).

Fairly recently, numerous immunoassay techniques have been developed which obviate the separation step through the use of a label whose detectable signal is modulated upon binding of the labeled reagent by a binding partner, e.g., antibody. Such techniques have become known as homogeneous and are advantageous when used in the present invention because separations are not required and radioisotopes are not involved. Some such techniques are fluorescence quenching and enhancement (see U.S. Pat. No. 4,160,016), energy transfer immunoassay (see U.S. Pat. No. 3,996,345), and double antibody steric hindrance immunoassay (see U.S. Pat. Nos. 3,935,074 and 3,998,943). Particularly preferred homogeneous immunoassay techniques are those employing a label which is a participant in an enzyme-catalyzed reaction. Examples are the substrate-labeled immunoassay (see U.S. Pat. No. 4,279,992 and U.K. Patent Spec. 1,552,607), the prosthetic group (FAD)-labeled immunoassay (see U.S. Pat. No. 4,348,565), the enzyme modulator-labeled immunoassay, e.g., using inhibitor labels (see U.S. Pat. Nos. 4,134,972 and 4,273,866), and enzyme-labeled immunoassay (see U.S. Pat. No. 3,817,837).

The monoclonal antibodies of the present invention are specific for binding to the glycosylated peptide residue comprising lysine 525 in human albumin. It may be required in some cases, or may be particularly desirable to improve assay performance, to expose the glycosylated lysine 525 epitope in the native albumin molecule in order to perform the desired immunoassay. Preferred antibodies produced in the manner described above will particularly require denaturation of sample glycoalbumin in order to bind. Steric access to the epitope can be obtained in any effective manner. Exposure of the epitope in the intact protein is understood to be accomplished by a physical or chemical denaturation or digestion at least in the region of the epitope. Such denaturation or digestion can be localized to the region of the epitope or can involve a more general, or even substantially complete denaturation of the tertiary, and additionally the secondary, structure of the protein, or partial or complete digestion of the protein.

When necessary or desirable, denaturation can be accomplished in a variety of ways including conventional treatment of the protein by physical means such as heat, sonication, high or low pH, adsorption to a solid surface such as plastic, and, as is preferable, chemical denaturation by interaction with a chaotropic agent or chaotrope in solution. Useful chaotropic agents will normally include, without limitation, guanidine, urea, various detergents such as sodium dodecylsulfate (SDS) and others, without limitation, including deoxycholate and certain bile salts, 3-(3-cholamidopropyl)-dimethylammonio-1-propanesulfonate, organic solvents such as methanol, propanol, acetonitrile and certain salts such as thiocyanate, e.g., the sodium, potassium and ammonium salts. Non-ionic detergents such as Triton X-100, nonidet NP-40 and octyl-glucosides can also function as protein denaturants. Inclusion of reagents (e.g., mercaptoethanol or dithiothreitol) that reduce disulfide bonds can be effective promoters of the denaturation process. When used without other denaturants, such reducing agents will break disulfide bonds which alone can be sufficient in certain cases to expose optimally the epitope. Protein denaturation can usually be most effectively accomplished if combinations of chemical and/or chemical and physical means are used (e.g., guanidine and heat, guanidine and SDS, or guanidine and dithiothreitol). Although generally less desirable, denaturation can also be achieved, as is known, by adsorption of protein to a solid surface such as a polymer surface. Such polymers will include synthetic, naturally occurring and modified naturally occurring polymers, e.g., polystyrene and celluloses, such as carboxy-methyl cellulose. Once sufficient denaturation is achieved by exposure to the denaturing conditions or agent, the conditions can be changed or denaturant removed, provided that the protein remains trapped in its denatured state. Of course, denaturing conditions which result in substantial insolubilization, aggregation, or precipitation of the protein such that an insignificant amount of the exposed epitope is accessible to the solution for antibody binding will be avoided. A sufficient amount of the denatured protein must remain in solution or suspension in order to obtain useful immunobinding. The extent of solubilization necessary will depend upon the circumstances of the intended or desired binding.

The present invention will now be illustrated, but is not intended to be limited, by the following examples.

EXAMPLES

EXAMPLE 1

Isolation of Naturally Occurring Albumin and Glycoalbumin

Whole blood from a normal human donor was collected into a citrate-dextrose solution and separated into red cells and plasma by centrifugation. The plasma fraction was chromatographed on a 100 ml boronate-agarose column (Glycogel, Pierce Chemical Co., Rockford, Ill., USA) in 0.25M ammonium acetate, 50 mM $MgCl_2$, pH 8.0. The bound fraction (containing primarily glycoalbumin and immunoglobulins) was eluted with 0.1M Tris, 0.2M sorbitol, 10 mM EDTA, pH 8.0. To separate glycoalbumin from immunoglobulins, the bound fraction was dialyzed into 50 mM sodium phosphate, ph 8.0, and loaded onto a 100 ml DEAE Affi-gel blue column (Bio-Rad Laboratories, Richmond, Calif. USA). The column was eluted with 50 mM sodium phosphate buffer, pH 8.0, containing a gradient of zero to 1.4M NaCl. The eluate was monitored at 280 nm and the glycoalbumin identified by SDS-polyacrylamide gel electrophoresis. In some experiments the plasma was chromatographed on DEAE Affi-gel blue before the Glycogel column. The order of separation does not effect the final purity of the albumin or glycoalbumin.

Non-glycosylated albumin was purified from the Glycogel non-bound fraction subsequently separated on a DEAE-affi-gel blue column as above. The albumin and glycoalbumin were dialyzed into phosphate buffered saline (PBS, 7.2 mM $Na_2HPO_4$, 2.8 mM $NaH_2PO_4$, 127 mM NaCl, pH 7.4) containing 0.05% sodium azide, lyophilyzed and stored at $-80°$ C. until further use.

EXAMPLE 2

Generation and Isolation of Enzymatically Cleaved Glycopeptides from Glycoalbumin Human serum albumin has 59 lysine residues, one of which is the primary site of glycosylation in the native molecule. To produce a peptide containing the glycosylated lysine (at position 525) we have used the known protein sequence of albumin coupled with the unique specificity of the two proteases trypsin and Staphylococcus aureus V8 protease. Trypsin cleaves the peptide bond on the carboxy-side of lysine and arginine, but does not cleave on the carboxy-side of a glycosylated lysine. Staph V8 cleaves on the carboxy-side of aspartic acid and glutamic acid. Therefore a tryptic digest or a V8 digest should produce the respective peptides containing the glycosylated lysine at position 525 [see Structures (1) and (2) in the drawing—the solid and open triangles indicate the cleavage sites for trypsin and V8 protease, respectively].

In its native conformation albumin is substantially resistent to proteolysis. To optimally expose the protein to the proteases glycoalbumin was denatured in 8M urea, 5 mM dithiothreitol (DTT), 0.1M ammonium bicarbonate, pH 7.85, for 2 hours at ambient temperature. The denatured protein solution is slowly added to 0.1M ammonium bicarbonate, pH 7.85, containing 1:50 ratio (weight of enzyme: weight of glycoalbumin) of protease to protein. The resulting final concentration of urea is 0.8M and the solution is maintained at 37° C. for 16 hours. Enzyme (equivalent in weight to the first addition) is then added and the solution incubated for 8 hours. The solution is applied to a boronate Affi-gel 601 column (BioRad, Richmond, Calif., USA) to selectively bind the carbohydrate containing peptides. The column is thoroughly washed in 50 mM ammonium bicarbonate and the bound peptides eluted with 0.1M acetic acid. The eluted peptides were dried, resuspended in 20 mM potassium phosphate, pH 7.0, and injected onto an Altex-ODS (4.1 mm×25 cm) HPLC column (Rainin, Emeryville, Calif., USA). A gradient of 1% acetonitrile/minute to a final concentration of 60% acetonitrile in the above buffer was used to elute the bound components. Fractions were collected, dried, and hydrolyzed under argon for 24 hours in 6N HCl containing 0.02% phenol. The hydrolysates were dried and analyzed using an OPA precolumn derivitization procedure (Benson and Hare, Proc. Natl. Acad. Sci. 72:619-622, 1975) and separation of the amino acid-OPA adducts on HPLC C-18 column (Supelco, Bellefonte, Pa., USA). Amino acids were identified and quantitated by comparison to known standards (Standard H; Pierce Chemical Co., Rockford, Ill., USA). The expected and found values for the tryptic and V8 peptides are shown in Table 1.

TABLE 1

| STAPH V8 PROTEASE PEPTIDE | | |
|---|---|---|
| AMINO ACID | EXPECTED | FOUND |
| GLU | 3 | 3.1 |
| THR | 1 | 1.0 |
| ARG | 1 | 1.2 |
| ALA | 1 | 1.0 |
| VAL | 1 | 1.0 |
| ILE | 1 | 0.7 |
| LEU | 1 | 1.0 |
| LYS | 2 | 1.9 |
| GLU | 2 | 2.1 |
| THR | 1 | 1.0 |
| ALA | 1 | 1.2 |
| VAL | 2 | 1.8 |
| LEU | 2 | 2.0 |
| LYS | 2 | 2.0 |

EXAMPLE 3

Coupling of Proteolytically Cleaved Glycopeptides to Carrier Protein

The C-terminal carboxylic acid was selectively activated and coupled to the amines of carrier proteins (Cell 34:587-596, 1983). Two mgs of EDCI (1-ethyl-3-(3-dimethylaminopropyl)-carbodiimide, Pierce Chemical Co.) in 200 μl of 0.01N HCl was added to 2 mg of the dry glycopeptide of Example 1. This solution was quickly added to 6 mg keyhole limpet hemocyanin (KLH) in 2 mL H2O resulting in a precipitate. The pH of the solution was raised to 9.0 with 0.1M ammonium carbonate, stirred for 3 hours and then dialyzed against PBS. The thiobarbituric acid test (Fluckinger and Winterhalter, FEBS Letters 71:356-360, 1976) indicated at least 2 carbohydrates/100,000 MW of KLH using fructose as the standard.

EXAMPLE 4

Chemical Synthesis of Albumin Peptides (a) Peptides were synthesized on the Applied Biosystems 430A Peptide Synthesizer (Applied Biosystems, Foster City, Calif., USA).

The carboxyl terminus amino acid was coupled to the resin by a phenylacetamidomethyl linkage with a substitution of 0.7 mmoles per gram resin. Typically 0.5 mmol of peptide was produced per synthesis. The N-terminal t-BOC was removed with 60% trifluoroacetic acid (TFA) in dichloromethane (DCM) and the α-amine neutralized with 10% diisopropylethylamine in dimethylformamide (DMF). t-BOC amino acids (2 mmol) were converted to preformed symmetrical anhydrides by the addition of 1 mmole dicyclohexylcarbodiimide in 2 ml dichloromethane. The side chains of the t-BOC amino acids were protected as follows: Arg(TOS), Asp(OBzl), Cys(4-CH Bzl), Glu(OBzl), His(TOS), Lys(Cl-Z), Ser(Bzl), Thr(Bzl), and Tyr(Br-Z). The t-BOC amino acids Ala, Asn, Gln, Gly, Ile, Leu, Met, Phe, Pro, Trp, and Val were not protected. The dicyclohexylamine salt of t-BOC-L-His(Tos) was converted to the free acid by ion-exchange on AG-50-X8(H+) resin (Bio-Rad) within one hour of coupling. The t-BOC amino acid Asn, Arg, and Gln (2 mmol) were coupled using preformed hydroxybenztriazole (HOBt) active esters formed by the addition of 2 mmol HOBt and 2 mmol DCC. The N-terminal t-BOC was removed from the completed peptide and the peptide resin dried overnight in vacuo.

The peptides were fully deprotected and cleaved from the resin by treatment with anhydrous HF containing 10% anisole for 60 minutes at 0° C. The resin was washed with ethyl acetate and the peptide extracted from the resin with 1.0N acetic acid. The extract was immediately frozen in liquid nitrogen, lyophilized, and stored at −20° C. until further use.

(b) ALB K14C LYS-GLU-ARG-GLN-ILE-LYS-LYS-GLN-THR-ALA-LEU-VAL-TYR-CYS

This 14 amino acid peptide has a 12 amino acid albumin sequence with a penultimate TYR and a C-terminal CYS. The sulfhydryl of the CYS can be selectively coupled to carriers or to fluorescent reagents (see Examples 6 and 9). During in vitro glycosylation the N-terminal and ε-amino groups of the N-terminal lysine are likely to be glycosylated [see structure (3) in the drawing]. However, proteolytic digestion with V8 will remove the terminal LYS-GLU or digestion with trypsin will remove the terminal LYS-GLU-ARG resulting in a shorter peptide which lacks the potentially glycosylated N-terminal lysine.

(c) ALB C11L CYS-GLU-ARG-GLN-ILE-LYS-LYS-GLN-THR-ALA-Leu

This peptide has 10 amino acids of the albumin sequence plus an N-terminal CYS for selective coupling. The N-terminal amino group of CYS is likely to be glycosylated but since it is proximal to the carrier or label it should not have an effect on the production of antibodies specific for glycoalbumin [see structure (4) in the drawing]. This peptide lacks the C-terminal hydrophobic amino acids VAL and TYR and has better solubility in aqueous and pyridine buffers.

(d) ALB Q12C GLN-ILE-LYS-LYS-GLN-THR-ALA-LEU-VAL-GLU-LEU-CYS

This peptide has 11 amino acids of the albumin sequence plus a C-terminal CYS for selective coupling [see structure (5) in the drawing]. The desired lysine epitope (525) has been placed 4 amino acids from the N-terminus increasing its exposure and its antigenicity.

(e) ALB R11E ARG-GLN-ILE-LYS-LYS-GLN-THR-ALA-LEU-VAL-GLU

This peptide has 11 amino acids of the albumin sequence [see structure (6) in the drawing]. The N-terminal ARG can be removed using trypsin if the N-terminal amino group becomes glycosylated during in vitro glycosylation. The desired lysine epitope (525) will be 4 amino acids from the N-terminus increasing its exposure and antigenicity. This peptide also has good solubility in aqueous and pyridine buffers.

(f) ALB Q9C LYS-GLN-THR-ALA-LEU-VAL-GLU-LEU-VAL-CYS

N-t-BOC-L-Lysine (Sigma Chemical Co., St. Louis, Mo., USA) was incubated in 95% pyridine, 5% acetic acid or 10% pyridine in absolute methanol saturated with glucose for 7 days at 50° C. The solution was dried to a syrup and N-t-BOC-$\epsilon$-1-deoxyfructosyl lysine purified by HPLC on a C-18 (Altex ODS, 4.1 mm×25 cm) column (Solvent A=50 mM triethylamine-acetate pH 6.0; solvent B=A:acetonitrile 50:50). The product has an Rf of 0.81 silica gel using chloroform:methanol:acetic acid (14:5:1) and was not reactive to amine detecting reagents unless briefly exposed to HCl vapors and heating to 100° C.

The N-t-BOC-$\epsilon$-1-deoxyfructosyl lysine is coupled to the N-terminus of the synthesized peptide GLN-THR-ALA-LEU-VAL-GLU-LEU-VAL-CYS. This peptide has eight amino acids of the albumin sequence plus a C-terminal CYS for coupling [see structure (7) in the drawing]. Following removal of t-BOC the resulting peptide has lysine 525 glycosylated solely on the $\epsilon$-amino group. For coupling, 1 equivalent of N-t-BOC-$\epsilon$-deoxyfructosyl lysine in dichloromethane is reacted with 0.5 equivalent dicyclohexylcarbodiimide for 15 minutes at room temperature under argon. An equal volume of dimethyl formamide is added followed by 0.25 equivalent moles of the synthesized peptide. After 30 minutes the solution is dried, resuspended in 25% TFA in dichloromethane for 30 minutes, dried again and the product purified on HPLC on a C-28 column.

(g) Tryptic condensation of the glycosylated product of ALB Q9C ($AA_1$) with $AA_2$.

The N-terminal extension peptide B-GLN-ILE-LYS is synthesized by conventional solution or solid phase peptide synthesis. The HPLC purified peptide is incubated with TPCK-treated trypsin (Cooper Biomedical, Malvern, Pa., USA) in 30% isopropanol or other suitable organic solvent (Fruton, Advances in Enzymology 53:239-306, 1981) and equal molar amounts of LYS-GLN-THR-ALA-LEU-GLU-LEU-VAL-CYS (the product of example 4f) are added. After twenty four hours the resulting product B-GLN-ILE-LYS-LYS-GLN-THR-ALA-LEU-VAL-GLU-LEU-VAL-CYS is isolated by HPLC. The terminal blocking group (B) can be removed by procedures that do not affect the 1-deoxyfructosyl residue on lysine 525.

(h) ALB Q7C LYS-GLN-THR-ALA-LEU-TYR-TYR-CYS

This peptide is used in experiments analogous to those described for (f) ALB Q9C where N-t-BOC-$\epsilon$-1-deoxyfructosyl lysine is coupled to the N-terminal GLN using dicyclohexylcarbodiimide as described in (f). This peptide (ALB Q7C) has at the C-terminus a TYR-TYR-CYS structure which is thought to potentiate the immune response against a synthetic peptide immunogen. The small size of the albumin part of the sequence (5 amino acids) should provide an epitope of restricted size and thereby focus the immune response to the glycosylated lysine residue.

(i) ALB K8C LYS-GLN-THR-ALA-LEU-TYR-TYR-CYS

ALB K8C is a small peptide-containing the desired glycosylated lysine on the N-terminus and the non-albumin TYR-TYR-CYS sequence at the C-terminus. This peptide is highly soluble in 0.1% TFA and absolute methanol which allow it to be purified by HPLC and glycosylated in the respective solvents.

(j) ALB K9C LYS-LYS-GLN-THR-ALA-LEU-TYR-TYR-CYS

ALB K9C has the properties of ALB K8C plus an additional lysine residue at the N-terminus.

(k) ALB I10C ILE-LYS-LYS-GLN-THR-ALA-LEU-TYR-TYR-CYS

ALB I10C has the properties of (j) ALB K9C but has an additional ILE residue at the N-terminus.

(l) ALB Q11C GLN-ILE-LYS-LYS-GLN-THR-ALA-LEU-TYR-TYR-CYS

ALB Q11C has the properties of (k) I10C but has an additional GLN residue at the N-terminus. This 11 amino acid peptide has an 8 amino acid albumin sequence and a 3 amino acid linking sequence (Tyr-Tyr-Cys). The Tyr-Tyr coupled to the C-terminal of the albumin sequence increases the inherent antigenicity of the albumin peptide. The C-terminal Cys was added to facilitate coupling to carrier molecules using conventional sulfhydryl-specific linking reagents. The desired lysine epitope (525) has been placed 4 amino acids from the N-terminus.

The ALC Q11C peptide has good solubility in 0.1% TFA and can be readily purified by HPLC. Typically 100 mg of crude peptide in 0.1% TFA is injected onto a Dynamax C-18 column (2.5×25 cm). A two hour gradient form 0.1% TFA to 0.1% TFA in 50% acetonitrile was used to elute the bound material. The peak fractions were analyzed by amino acid analysis and the fraction that yielded the expected molar rates of amino acids for Q11C was lyophilyzed and stored at −80° C.

(m) ALB C10T CYS-TYR-TYR-ARG-GLN-ILE-LYS-LYS-GLN-THR

ALB C10T was synthesized with the non-albumin sequence (CYS-TYR-TYR) on the N-terminus to favor antibodies that may bind preferentially to the glycosylated lysine and the C-terminal sequence of this peptide.

EXAMPLE 5

Glycosylation of synthetic peptides

The four synthetic peptides listed in Table 2 were glycosylated as indicated. The Q9C peptide was prepared by glycosylation as described in Example 4(f).

TABLE 2

|  | K14C | C11L | Q12C | R11E |
| --- | --- | --- | --- | --- |
| (a) pyridine, 0.25M glucose | + | + | + | + |
| (b) 50% pyridine, 50% H$_2$O, 0.125M glucose | + |  | + | + |
| (c) PBS, 1.0M glucose | + | + | + | + |
| (d) 95% pyridine, 5% acetic acid 0.25M glucose, pH 7.0 | + | + | + | + |

Reactions were from ambient to 50° C. and from 1-20 days. Samples were dried to a syrup and injected onto an Altex C-18 (1×25 cm) using a 0.1% TFA to 0.1% TFA, 60% acetonitrile gradient. Peak fractions were collected, analyzed for carbohydrate and used in the production of glycopeptide-MBS-carrier protein immunogens.

The non-glycosylated peptides were also coupled to KLH-MBS and subsequently glycosylated in vitro in PBS containing 1.0M glucose (pH 9.5 or 7.4) at 37° C. for 7-14 days. Thiobarbituric acid analysis indicated 10-40 carbohydrates/100,000 MW KLH.

Peptides of Example 4 (i) through (m) were glycosylated at elevated temperatures (50°-80° C.) 70° C. in glucose saturated methanol for 24 hours. The methanol was removed by negative pressure and the glycopeptide purified by HPLC. This has been shown to be highly effective in attaching glucose to the lysine amino groups in synthetic peptides and to the N-t-BOC-L-LYSINE of Example 4 (f).

Glycosylation of N-t-BOC-L-LYSINE in glucose saturated methanol 50°-80° C. for 24 hours was especially effective. Sequence analysis (Example 6 below) identified the product (after removal of the α-amine protecting group) as ε-deoxyfructosyl lysine. Fast atom bombardment mass spectrascopy also gave the predicted molecular weight of the glycoslyated N-t-BOC-L-LYSINE derivative.

EXAMPLE 6

Sequence analysis for the determination of the position and quantitation of glycosylated lysines A method was developed for the determination of the position and the quantitation of glycosylated lysine residues using automated gas-phase Edman degradation sequencing procedures. During conventional sequence analysis both amino groups on lysine are reactive with PITC (phenylisothiocyanate) forming a lysine with a PTC group (phenylthiocarbamyl) on the ε-amino group and a PTH (phenylthiohydantoin) on the α-amino group. A glycosylated lysine, however, will not have the PTC group on the ε-amino because the carbohydrate blocks that amine from reacting with PITC.

The lysine product is therefore PTH-lysine. In the sequence analysis of the naturally occurring glycoalbumin peptides of Example 2 applicants have identified the PTH-lysine residue since it has a unique chromatographic retention time on the C-18 reverse phase column used to separate and quantitate the various PTH-amino acids. All glycosylated synthetic peptides were sequenced to identify the particular glycosylated lysine in multi-lysine peptides and to quantitate the ratio of lysine to glycolysine. The results indicate that greater than 75% of the lysines have the correct glycosylation reaction product on lysine when the glycosylation is done in methanol.

EXAMPLE 7

Coupling of synthetic glycopeptides to carrier proteins

Synthetic glycopeptides containing CYS are coupled to carriers as described by Lerner et al (Proc. Natl. Acad. Sci. 78: 3403, 1981). Briefly KLH is reacted with a 50-fold molar excess of sulfo-MBS (Pierce Chemical Co.) for 25 minutes at ambient temperature in 50 mM sodium phosphate, pH 6.2, and the KLH-MBS conjugate separated from unreacted sulfo-MBS by gel filtration in the same buffer. The KLH-MBS conjugate was immediately added to the dried glycopeptide (2-fold molar excess of glycopeptide to maleimide of carrier) and reacted overnight at room temperature.

For peptides lacking CYS, the C-terminal carboxylic acid was coupled to the amino groups of carrier proteins as described in Example 3.

EXAMPLE 8

Immunization

The selected glycopeptide MBS-KLH conjugate of Example 7 was emulsified with an equal volume of Freund's complete adjuvant. Mice (BALB/cBy), preferably 6-8 weeks old, were injected with 200 μg of conjugate and were boosted at 30 and 60 days with conjugate in incomplete adjuvant. Three days prior to fusion mice were injected with 50 μg IV. The mice were sacrificed and their spleens used for fusions according to Kohler and Milstein, Nature 256:495 (1975).

EXAMPLE 9

Screening of hybridoma supernatants for antibodies specific for glyco-albumin (a) ELISA assay Albumin and glycoalbumin of Example 1 were heated to 60° C. for 15 minutes, preferably in PBS containing 3.0M guanidine hydrochloride and 7 mM beta-mercaptoethanol and coated onto separate polystyrene microtiter plates (2 μg per 100 microliters/well) overnight at 4° C. Alternatively, native glycoalbumin can be coated onto microtiter plates and subsequently denatured in 3.00M guanidine hydrochloride containing 7 mM beta-mercaptoethanol. Plates were washed with PBS, 0.05% Tween-20. Supernatants from each cell line were incubated in albumin or glycoalbumin coated plates for 60 minutes. The plates were washed 4 times with PBS+0.05 Tween-20 and 200 microliters of secondary antibody added to each well (1:2000 dilution of rabbit anti-mouse IgG-peroxidase, Miles Laboratories, Inc., Elkhart, Ind, USA). After 60 minutes the plates were washed 4 times in PBS+0.05% Tween and 200 microliters of substrate solution (24.3 mM citric acid, 51.4 mM sodium phosphate, pH 5.3, containing 2.2 mM o-phenylenediamine and 5.2 mM hydrogen peroxide) was added. The reaction was terminated after 20 minutes by adding 50 microliters of 8M $H_2SO_4$ and the product of the peroxidase reaction read at 492 nm. The monoclonal antibodies that are specific for glycoalbumin react with glycoalbumin and not albumin.

Positive hybridomas were cloned by a limiting dilution technique. A glycoalbumin specific cell line was obtained using the preferred peptide ALB Q11C as the immunogen, immunization of young mice and screening of hybridomas with denatured glycoalbumin and has been deposited with the American Type Culture Collection as ATCC No. HB 9644, deposited Feb. 11, 1988.

(b) Particle concentration fluorescent immunoassay

Albumin and glycoalbumin (the latter being predenatured or native depending on the requirements of the antibody) were coated onto separate polystyrene particles (Pandex Laboratories, Mundelein, Ill., USA). Hybridoma supernates (20 microliters) were added to each well followed by 20 microliters of albumin or glycoalbumin coated particles. After 30 minutes a 1:5000 dilution of goat anti-mouse IgG-FITC (see Example 10) was added and the incubation continued for an additional 30 minutes. All the non-bound reactants were removed by filtration and the fluorescence measured. In a specific response, antibodies in the hybridoma supernate bind to glycoalbumin but not albumin coated particles.

(c) Particle concentration fluorescent immunoassay with prior dissociation of albumin/glycoalbumin from monoclonal antibody Goat anti-mouse particles (Pandex Laboratories) are incubated with hybridoma supernates to capture the mouse antibodies. A percentage of mouse monoclonal antibodies are bound to the naturally occurring glycoalbumin in the cell culture media used to grow the hybridoma cells. Non-bound components are separated by filtration leaving the goat anti-mouse particles, with bound mouse immunoglobulins from the hybridoma media and in turn the glycoalbumin bound to the mouse immunoglobulin. Twenty (20) microliters of 100 mM glycine, pH 3.0, is added to dissociate all complexes. Twenty minutes later, 20 microliters of 50 mM Tris base containing glycoalbumin (denatured or native) labeled with fluorescein using the sulphydryl specific fluorescein-5-maleimide is added. The resulting pH of 7.5 renatures the mouse immunoglobulin which preferentially binds to the excess of fluorescent glycoalbumin. The mouse immunoglobulin-fluorescent glycoalbumin complex is captured by the existing goat anti-mouse particles or by adding fresh goat anti-mouse Ig particles. The non-bound reagents are removed by filtration and the signal is proportional to the mouse anti-glycoalbumin antibodies present in the hybridoma supernate.

(d) Improved growth medium

Fetal calf serum (20%) used to maintain and grow myeloma cells and hybridoma cells has a significant concentration of bovine albumin and presumably glycoalbumin which is known to have the same amino acid sequence as human albumin surrounding thing glycosylated lysine at position 525. It is therefore highly probable that the small amount of anti-glycoalbumin antibodies secreted into the tissue culture media immediately bind to the glycosylated albumin molecules and cannot be detected in the standard ELISA assay.

To eliminate the binding of antibody to media glycoalbumin, myeloma cells and hybridoma cells were adapted to growth in serum (and albumin) free media. The media currently being used is commercially available (HL-1, Ventrex, Portland, Me. USA). The screening of hybridoma supernates in the HL-1 media simplifies the identification of clones secreting anti-glycoalbumin antibodies.

(e) Growth of hybridoma cells in glycoalbumin containing media

As discussed in Example 9 (d) the presence of glycoalbumin in the media may prevent the detection of anti-glycoalbumin specific antibodies. It is therefore necessary to remove the glycoalbumin from the media by a selection adsorption process. This is accomplished by selectively absorbing the albumin and glycoalbumin from fetal calf serum by passage down an Affi-Gel Blue column (BioRad Labs, Richmond, Calif., U.S.A.) using the manufacturer's directions. The albumin fraction has an affinity for the reactive blue dye under these conditions but can be eluted using 1.4M sodium chloride. The eluted fraction containing approximately 90% albumin and 10% glycoalbumin is applied to a Glyco-Gel B (boronate column-Pierce Chemical Co., Rockford, Ill., U.S.A.). This column selectively binds glycoalbumin. The non-bound fraction contains nonglycoalbumin and is added back to the Affi-Gel non-bound fraction which contains all serum components except albumin. The final mixture is fetal calf serum deleted of glycoalbumin and is used to prepare the media for the growth of hybridomas producing anti-glycoalbumin specific antibodies.

EXAMPLE 10

Fluorescent labeling of synthetic glycopeptides

The glycopeptides can be conveniently labeled using sulfhydryl specific fluorescein conjugates. A two fold molar excess of fluorescein-5-malemide in dimethylformamide (40 mg/ml) is added to glycopeptide (10 mg/ml) in 100 mM sodium phosphate, 5 mM EDTA, pH 7.1. The sample is incubated for 20 hours at room temperature. The glycopeptide-fluorescein conjugate is purified by HPLC on an Altex C-18 4.1 mm×25 cm column using 20 mM sodium phosphate to 20 mM sodium phosphate, 50% acetonitrile gradient.

EXAMPLE 11

Production of ascites and purification of the monoclonal antibodies

The cell line ATCC No. HB 9644, deposited Feb. 11, 1988 ($1 \times 10^6$ cell/mouse) was injected IP into pristane-primed Balb/cBy mice. The ascites was collected and sodium azide added to a concentration of 0.05%. The ascites solution was clarified by centrifugation (10,000×g, 60 minutes). Saturated ammonium sulfate was added to the ascites to a final concentration of 50%. The resulting solution was centrifuged at 3,000×g for 10 minutes and the resulting precipitated immunoglobulin fraction was suspended and dialyzed into 0.1M sodium borate pH 8.0. The immunoglobulin was further purified by HPLC gel filtration. Aliquots (2 ml) were injected onto Zorbax GF-250 columns (2 columns each 1.0×25 cm) in 0.1M $NaH_2PO_4$ at pH 7.0 at a flow rate of 1 ml/minutes. The eluate was monitored at 280 nm. Peak fractions were analyzed for glycoalbumin specific antibodies by ELISA assay (see Example 9). Peaks containing antibody activity were pooled, quantitated by UV absorbance and Lowry determinations and assayed for purity by SDS-polyacrylamide gel electrophoresis. The purified antibody was judged to be approximately 90% by these procedures.

EXAMPLE 12

Immunoassay for glycoalbumin in clinical specimens (A) Antibody specific for glycoalbumin is coated onto polystyrene particles (0.8 um) Pandex Laboratories). Antibody coated beads (20 microliters) are incubated with an appropriately diluted blood specimen, e.g., 1:800. The specimen may be serum, plasma or whole blood. The diluent may be in physiological buffers or in denaturing solutions that lyse red blood cells and optimally expose the glycoalbumin epitope. Following an appropriate incubation (e.g., 5 minutes), synthetic glycopeptide fluorescein conjugate (Example 10) is added to bind to unoccupied antibody binding sites on the particles. After a further incubation (e.g., 20 minutes), all non-bound reactants are removed by filtration and the fluorescein quantitated. The fluorescein signal is therefore inversely proportional to the amount of competing glycoalbumin in the clinical specimen.

(B) Sera from normal or diabetic individuals are added to microtiter plate wells (100 µl/well) and incubated for two hours at ambient temperature. The wells are washed with PBS and the bound proteins including glycoalbumin are denatured with 3.0M guanidine containing 7 mM beta-mercaptoethanol for 15 minutes at 60° C. (alternatively, an aliquot of sera can be denatured prior to addition to the microtiter well). The denaturants are washed form the plate and the bound % glycoalbumin quantitiated by the ELISA described in Example 9(a). The higher the percentage of glycoalbumin in the original sera, the greater glycoalbumin bound to the microtiter plate and thus the higher optical density produced by the secondary antibody-enzyme couplex in the ELISA assay. The percent glycoalbumin can be calculated by comparison to results obtained with albumin-glycoalbumin mixtures of Example 1.

EXAMPLE 13

The titer of purified anti-glycoalbumin specific antibody on glycoalbumin and non-glycoalbumin coated polystyrene plates Polystyrene microtiter plates were coated with purified albumin or glycoalbumin as described in Example 9. Purified monoclonal antibody (ATCC No. HB 9644, deposited Feb. 11, 1988) was serially diluted (2-fold) in PBS containing 0.05% Tween-20 and 1% gelatin (Bio-Rad) (PBST+GEL) and added to the albumin and glycoalbumin coated plates. After a two hour incubation, the plates were washed with PBST, incubated with secondary antibody-enzyme and the bound secondary antibody enzyme detected as described on Example 9. The results show that the glycoalbumin specific antibody binds to glycoalbumin coated plates but does not bind to non-glycoalbumin coated plates (FIG. 3).

EXAMPLE 14

Figure 4:
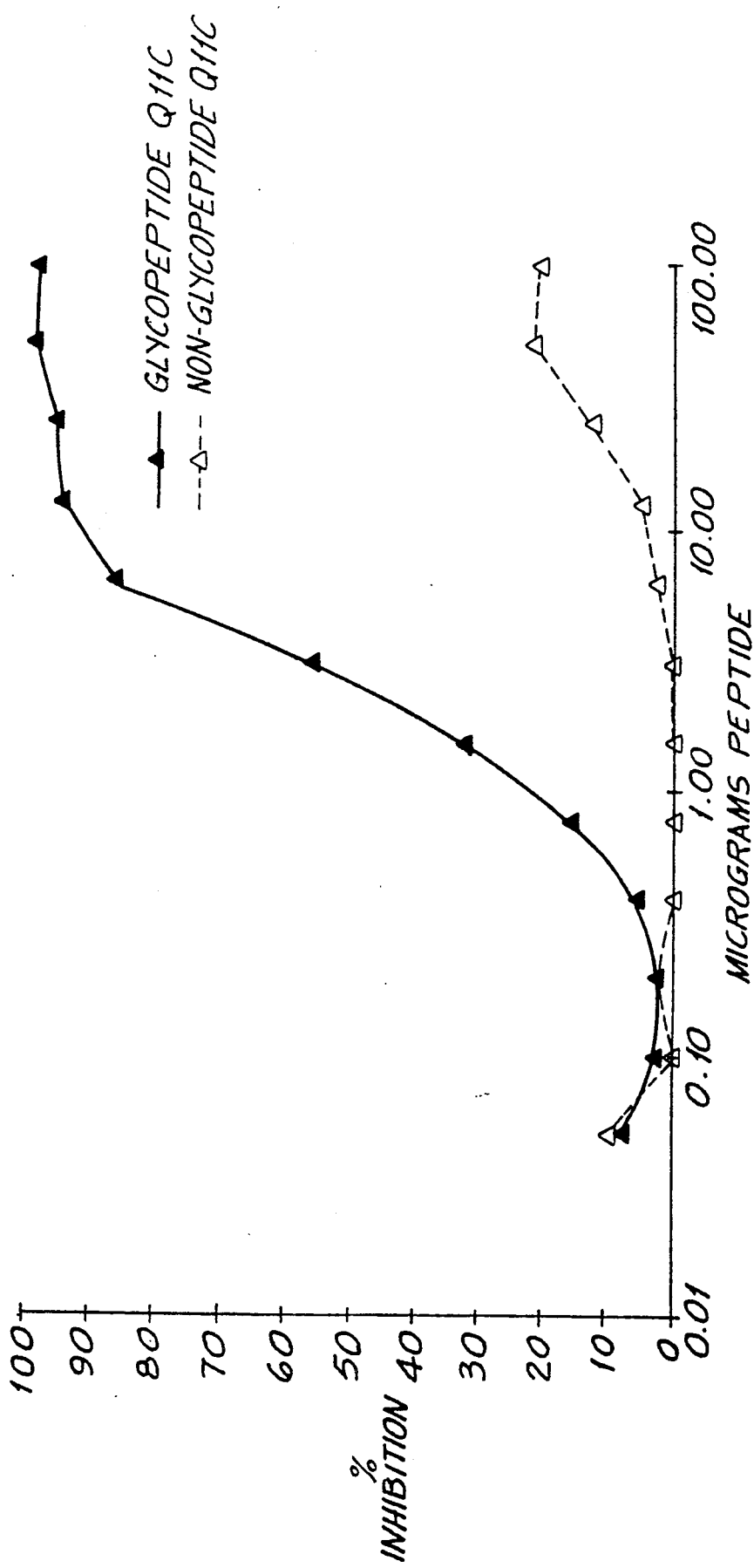

Synthetic peptide and glycopeptide inhibition of anti-glycoalbumin antibody binding to glycoalbumin Purified anti-glycoalbumin antibody (ATCC No. HB 9644, Feb. 11, 1988) at a dilution of 1:1000 in PBST+1% gelatin (final concentration of antibody 2.27 µg/ml) was preincubated with synthetic peptide or synthetic glycopeptide for one hour at room temperature. This solution was then transferred onto a glycoalbumin coated plate and incubated for two hours. The plate was then washed and processed for the detection of binding of anti-glycoalbumin antibody as described in Example 9. The results (FIG. 4) show that the glycopeptide can totally inhibit antibody binding to glycoalbumin whereas the non-glycopeptide inhibits binding to a maximum of 20% at a much higher concentration of peptide.

EXAMPLE 15

Quantitation of Percent Glycoalbumin by ELISA Assay

Figure 5:
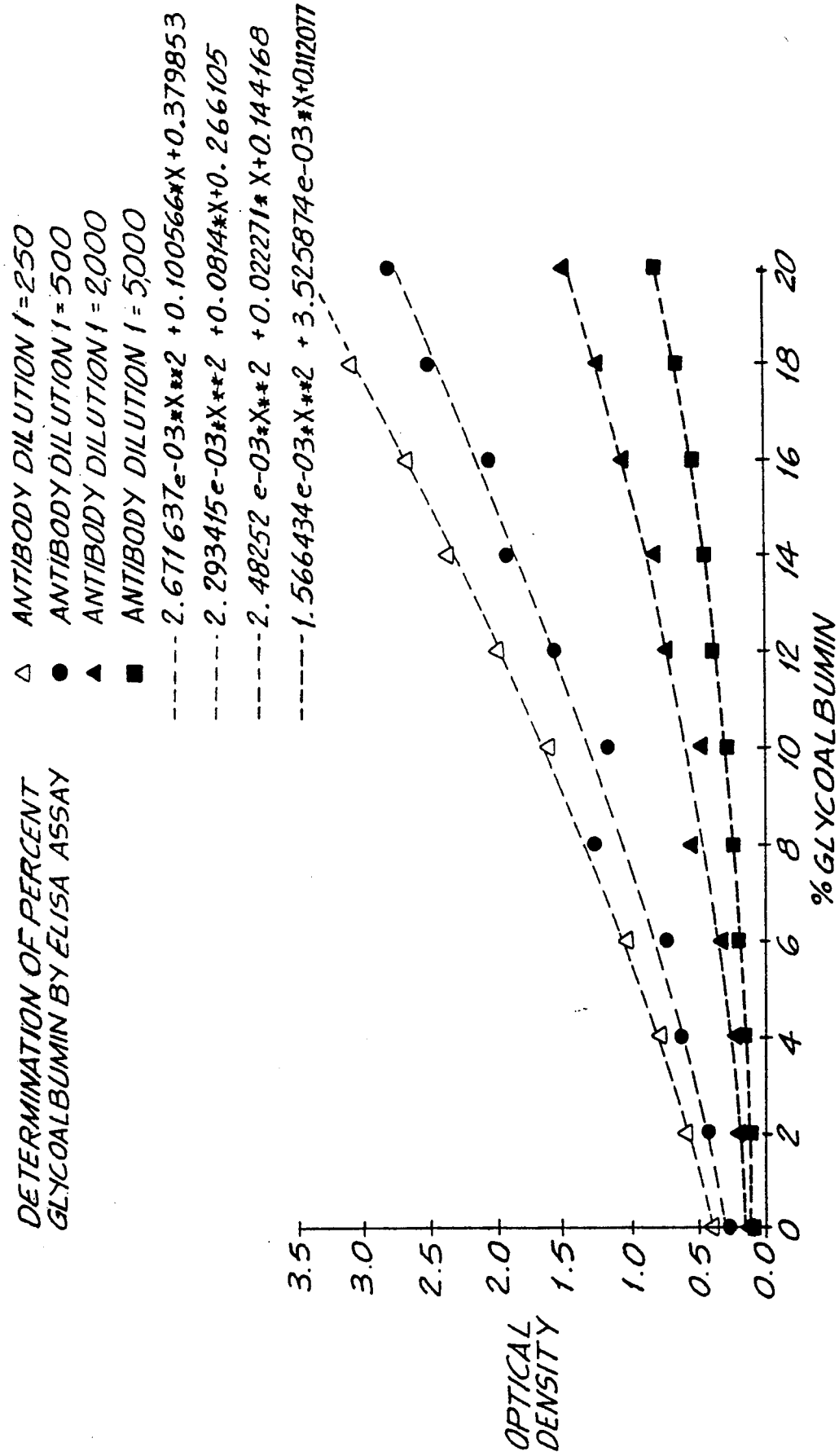

Purified albumin and glycoalbumin of Example 1 were mixed in varying ratios and coated onto microtiter plates as in Example 9. Purified anti-glycoalbumin specific monoclonal (ATCC No. HB 9644, deposited Feb. 11, 1988, 2.27 mg/ml) was diluted into PBST+1% gelatin (see FIG. 5 for dilutions) and added to the microtiter plate. Antibody binding was detected by the ELISA procedures of Example 9. The results (FIG. 5) indicate that the percent glycoalbumin can be determined by an ELISA using the glycoalbumin specific monoclonal antibody.

EXAMPLE 16

The Effect of Denaturant on the Immunoreactivity of Glycoalbumin

Figure 6:
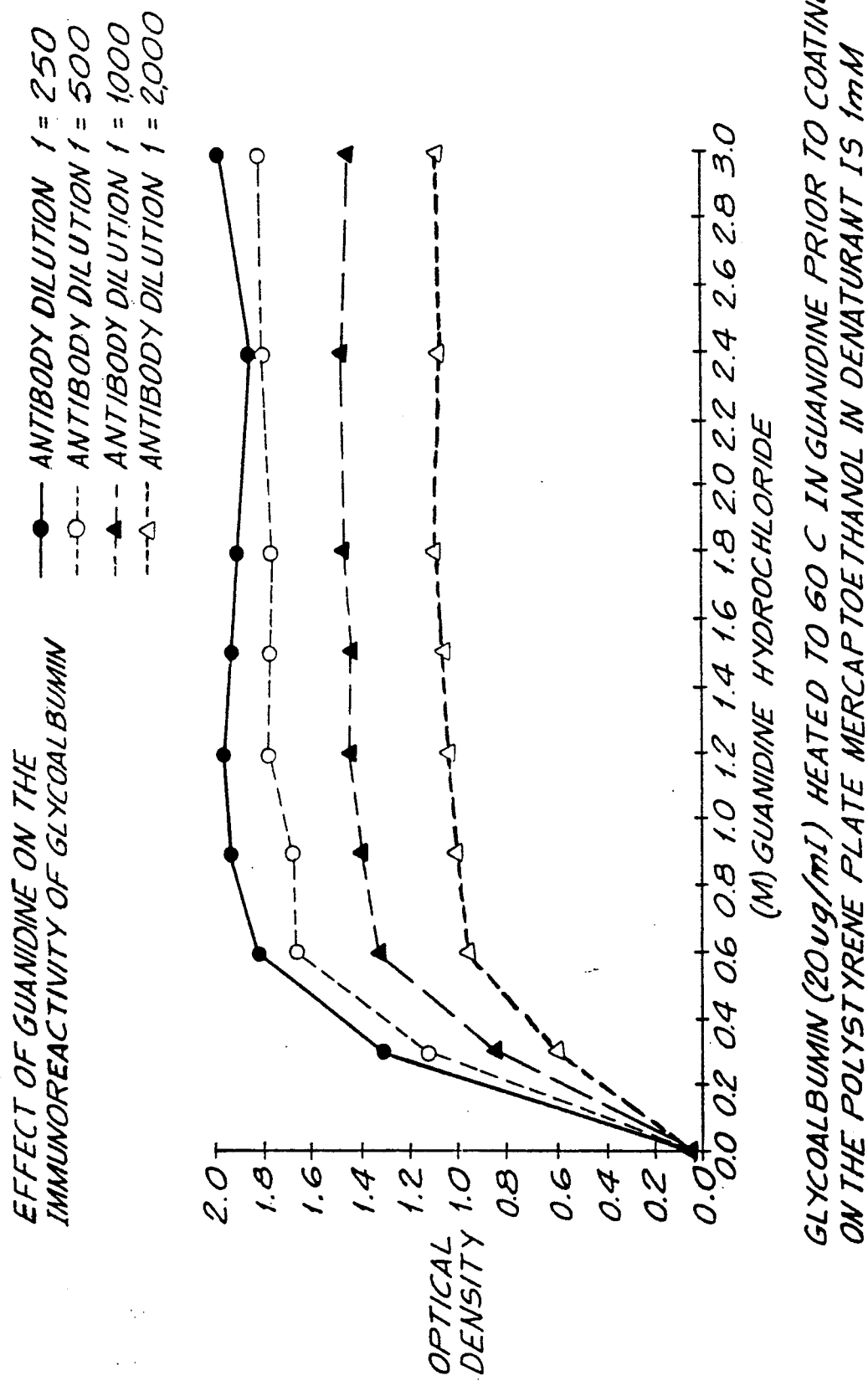

Purified glycoalbumin (20 mg/ml in PBS) was heated to 60° C. for 15 minutes in varying concentrations of guanidine hydrochloride containing 1 mM beta-mercaptoethanol. The solutions were then used to coat microtiter plates as described in Example 9. The purified monoclonal (ATCC No. HB 9644, deposited Feb. 11, 1988) at varying dilutions was used to detect immunoreactive glycoalbumin (FIG. 6). The quantitation of antibody binding was as described in Example 9. The results (FIG. 6) indicate that the glycoalbumin is preferably denatured in approximately 1M guanidine hydrochloride containing mercaptoethanol at 60° C. for 15 minutes in order to optimally expose the glycopeptide epitope.

EXAMPLE 17

Figure 7:
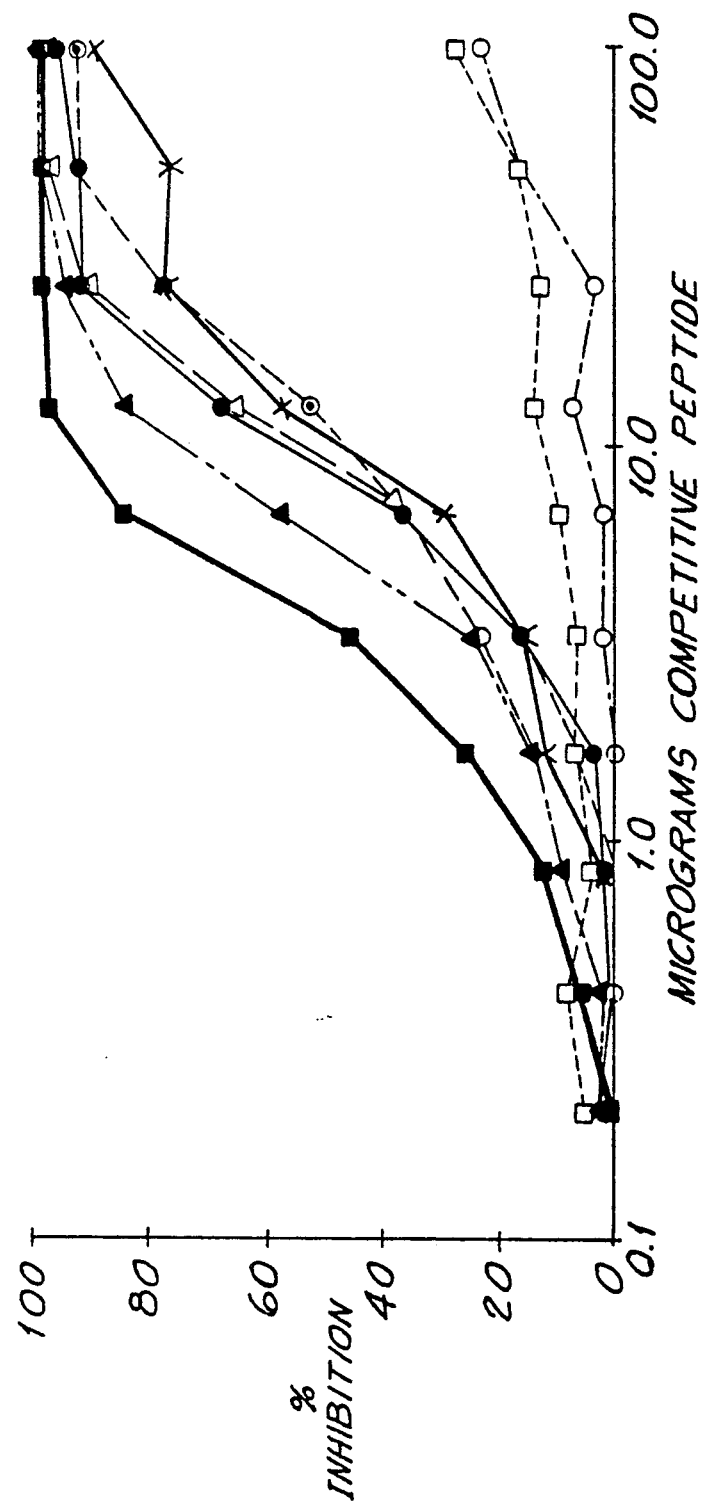

Synthetic Peptide and Glycopeptide Inhibition of Anti-Glycoalbumin Antibody Binding to Glycoalbumin Purified glycoalbumin (20 µg/ml) of Example 1 was coated onto polystyrene microtiter plates (Example 9). The synthetic peptides and glycopeptides (of FIG. 7) were preincubated for two hours at ambient temperature with a 1:1000 dilution of purified monoclonal antibody (ATCC No. HB 9644, deposited Feb. 11, 1988). This mixture was then transfered onto the glycoalbumin coated plate, incubated for one hour and antibody binding measured by the ELISA assay of Example 9. The results shown in FIG. 7 indicate that all glycopeptides bind to the antibody binding site. This would suggest that the epitope includes the glycosylated lysine 525 and only a few (2-3) amino acids on either the carboxy or amino terminal side. The non-glycosylated peptides show little competition indicating that the carbohydrate is an essential part of the epitope.

EXAMPLE 18

Figure 8:
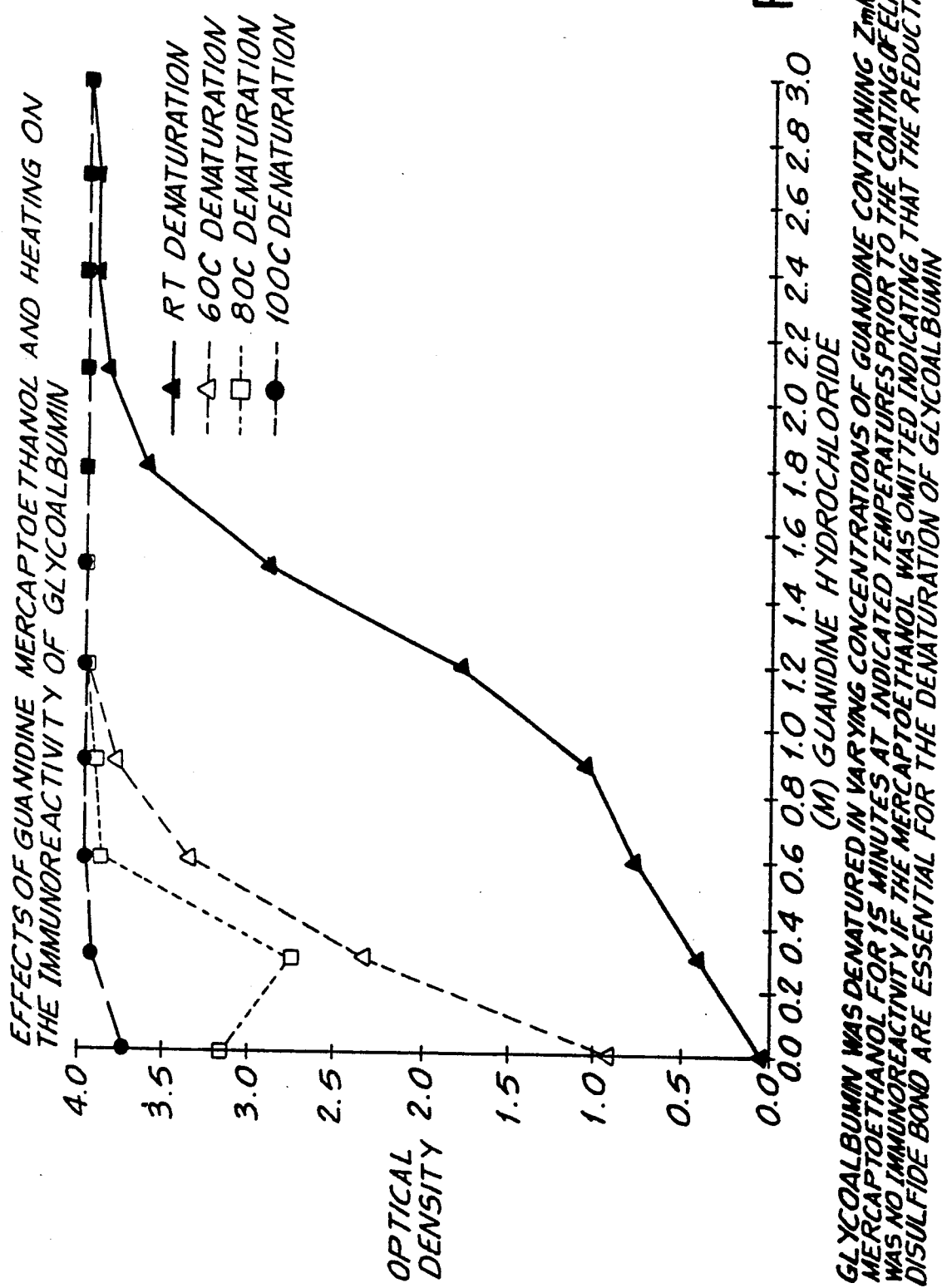

The Effect of Guanidine, Mercaptoethanol and Heat on the Immunoreactivity of Glycoalbumin Glycoalbumin was denatured in varying concentrations of guanidine containing 7 mM beta-mercaptoethanol at the temperature indicated in FIG. 8 prior to coating microtiter plates so described in Example 9. The binding of the monoclonal antibody (ATCC No. HB 9644, deposited Feb. 11, 1988) to the immobilized glycoalbumin was as described in Example 9. The results (FIG. 8) indicate that a combination of heat, mercaptoethanol and guanidine are preferred for exposing the glycoalbumin epitope. If the mercaptoethanol is omitted then there appears to be no immunoreactivity (data not shown) suggesting that the reduction of disulfide bonds is essential for the denaturation of glycoalbumin and exposure of these glycoalbumin epitope for binding to the monoclonal antibody ATCC No. HB 9644, deposited Feb. 11, 1988.

It will be understood that the specification and examples are illustrative, but not limiting with regard to the present invention and that other embodiments and modifications within the spirit and scope of the present invention will be evident to those skilled in the art.

What is claimed is:

1. An immunoassay method for determining glycosylated albumin in a human blood sample, comprising the steps of:
   (a) contacting the blood sample with a monoclonal antibody, or a fragment thereof comprising an antibody combining site, which binds specifically to human albumin at lysine residue 525, wherein said lysine residue is glycosylated, and wherein said monoclonal antibody does not bind substantially to any other proteins present in human blood; and
   (b) determining binding of said monoclonal antibody or fragment thereof to glycosylated human albumin as a function of the amount of glycosylated albumin in the sample tested.

2. The method of claim 1, wherein the blood sample is pretreated to denature a significant amount of any glycosylated albumin therein.

3. The method of claim 1, wherein the monoclonal antibody or fragment thereof binds specifically to a glycosylated peptide residue of the formula:

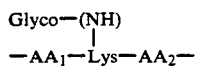

wherein Glyco-(NH) represents a nonenzymatically glycosylated ε-amino group in the lysine residue, and one or both of $AA_1$ and $AA_2$ is a sequence of amino acids wherein at least one of the amino acid units is in a position corresponding to the peptide sequence of human albumin adjacent to the lysine residue at position 525, and if only one of $AA_1$ and $AA_2$ is such a sequence, then the other is a bond or additional amino acid residues.

4. The method of claim 3, wherein one or both of $AA_1$ and $AA_2$ is a sequence of from 1 to 12 amino acids corresponding to the peptide sequence adjacent to the lysine residue at position 525 in human albumin.

5. The method of claim 1, wherein the monoclonal antibody has been raised against an immunogen comprising a glycosylated peptide chemically linked to an immunogenic carrier material, the glycosylated peptide comprising a lysine residue whose ε-amino group is nonenzymatically glycosylated and at least one other amino acid unit in a position corresponding to the peptide sequence of human albumin adjacent to the lysine residue at position 525.

6. The method of claim 5, wherein the immunogen is of the formula:

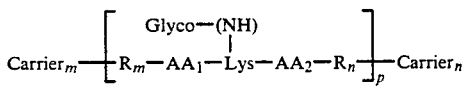

wherein Glyco-(NH) represents a nonenzymatically glycosylated ε-amino group in the lysine residue; one or both of $AA_1$ and $AA_2$ is a sequence of amino acids wherein at least one of the amino acid units is in a position corresponding to the peptide sequence of human albumin adjacent to the lysine residue at position 525, and if only one of $AA_1$ and $AA_2$ is such a sequence, then the other is a bond, a terminal amino or carboxyl group, or additional amino acid residues; R is a bond or linking group; Carrier is an immunogenic carrier material; one of $m$ and $n$ is 1 and the other is zero; and $p$ is on the average from 1 to the number of available coupling sites on Carrier.

7. The method of claim 6, wherein $AA_1$ is a terminal amino group, $AA_2$ is Gln-Thr-Ala-Leu-Val-Glu-Leu-Val-Lys, $m$ is zero, and $n$ is 1.

8. The method of claim 6, wherein $AA_1$ is (NH$_2$)Arg-Gln-Ile-Lys, $AA_2$ is Gln-Thr-Ala-Leu-Val-Glu, $m$ is zero, and $n$ is 1.

9. The method of claim 6, wherein $AA_1$ is (NH$_2$)Lýs-Glu-Arg-Gln-Ile-Lýs and $AA_2$ is Gln-Thr-Ala-Leu-Val-Tyr-Cys wherein Lýs is a glucosylated or non-glycosylated lysine unit, and wherein $m$ is zero and $n$ is 1.

10. The method of claim 6, wherein $AA_1$ is Cys-Glu-Arg-Gln-Ile-Lýs and $AA_2$ is Gln-Thr-Ala-Leu (COOH) wherein Lýs is a glycosylated or non-glycosylated lysine unit, and $m$ is 1 and $n$ is zero.

11. The method of claim 6, wherein $AA_1$ is Gln-Ile-Lys, Ile-Lys, Lys, or a terminal amino group; $AA_2$ is Gln-Thr-Ala-Leu-Tyr-Tyr-Cys; $m$ is zero, and $n$ is 1.

12. The method of claim 11, wherein $AA_1$ is Gln-Ile-Lys.

13. The method of claim 4, wherein $AA_1$ is Cys-Tyr-Tyr-Arg-Gln-Ile-Lys; $AA_2$ is Gln-Thr, $m$ is 1 and $n$ is zero.

14. The method of claim 11, wherein the blood sample is whole blood, serum or plasma.

* * * * *

UNITED STATES PATENT AND TRADEMARK OFFICE
CERTIFICATE OF CORRECTION

PATENT NO. : 5,225,354
DATED : July 6, 1993
INVENTOR(S) : Knowles, et al.

It is certified that error appears in the above-identified patent and that said Letters Patent is hereby corrected as shown below:

Col. 26, line 4    Delete

" $Carrier_m \left[ \begin{array}{c} Glyco-(NH) \\ | \\ R_m-AA_1-Lys-AA_2-R_n \end{array} \right]_p Carrier_n$ "

and substitute

-- $\underset{\sim}{Carrier_m} \left[ \begin{array}{c} Glyco-(NH) \\ | \\ \underset{\sim}{R_m}-AA_1-L\underset{\sim}{y}s-AA_2-\underset{\sim}{R_n} \end{array} \right]_{\underset{\sim}{p}} \underset{\sim}{Carrier_n}$ --

Col. 26, line 43   After " claim " delete " 11 " and substitute -- 1 --

Signed and Sealed this

Fourteenth Day of February, 1995

Attest:

BRUCE LEHMAN

*Attesting Officer*     *Commissioner of Patents and Trademarks*